United States Patent [19]

Russell et al.

[11] Patent Number: 4,722,330

[45] Date of Patent: Feb. 2, 1988

[54] FEMORAL SURFACE SHAPING GUIDE FOR KNEE IMPLANTS

[75] Inventors: Kenneth W. Russell, Maryland Heights; Leo A. Whiteside, Chesterfield, both of Mo.

[73] Assignee: Dow Corning Wright Corporation, Arlington, Tenn.

[21] Appl. No.: 855,016

[22] Filed: Apr. 22, 1986

[51] Int. Cl.$^4$ .............................................. A61F 5/04
[52] U.S. Cl. ......................... 128/92 VW; 128/303 R
[58] Field of Search ......... 128/92 V, 92 VY, 92 VW, 128/92 YL, 92 VV, 92 VD, 303 R

[56] References Cited

U.S. PATENT DOCUMENTS

| | | | |
|---|---|---|---|
| 4,457,307 | 7/1984 | Stillwell | 128/92 VY |
| 4,474,177 | 10/1984 | Whiteside | 128/303 R |
| 4,487,203 | 12/1984 | Androphy | 128/303 R |
| 4,502,483 | 3/1985 | Lacey | 128/303 R |

OTHER PUBLICATIONS

Data Sheet, "Whiteside ORTHOLOC (TM)Total Knee System—Surgical Procedure", Dow Corning Wright Corporation, Arlington, Tenn., No. L095-0201 9/85, 40 pages.
Data Sheet, "New Whiteside ORTHOLOC(TM) Total Knee Instruments"; Dow Corning Wright Corp., Arlington, Tenn., No. L095-PN003 (1985), 1 page.
Data Sheet, "ZIMMER(®) Intramedullary Knee Instrumentation For the Miller Galante Total Knee System", Zimmer, Inc., Warsaw, Ind., No. 86-038-0525/1-6MA (1986), 32 pages.
Brochure, "Knee Replacement Using The INSALL-/BURSTEIN Total Condylar Knee System", Zimmer, Inc., Warsaw, Ind., No. 81-038-226-1020/15MZ (1981), 24 pages.
Brochure, "R.M.C. Total Knee System—Technique", Richards Mfg. Co., Inc., Memphis, Tenn., No. 3246 Rev. 9-79 (1979), 37 pages.
Brochure, "The P.C.A.(TM) Primary Total Knee System", Howmedica Inc., Rutherford, N.J., No. H-21-31-115M 12/84 B (1984), 34 pages plus 72 pages Surgical Procedure.
Brochure, "GEO-PATELLA(TM)-/GEO-TIBIAL(TM) Total Knee—Surgical Technique", Zimmer, Inc., Warsaw, Ind., No. B-26-0-110M778 (1977), 34 pages.
Brochure, "Lacey Condylar Total Knee System—Surgical Procedures", Dow Corning Wright Corp., Arlington, Tenn.., No. L095-0204, 12 pages.
Data Sheet, "Dow Corning Wright Knee Instrumentation System", Dow Corning Wright Corporation, Arlington, Tenn., No. L095-0015 (Jan., 1982) 6 pages.
Brochure, "Surgical Technique Using AOR(TM) Total Knee Instrumentation For The MILLER/GALANTE Porous TIVANIUM(®) Total Knee System", Zimmer, Inc., 32 pages.
Brochure, "Use the MICROLOC(TM) Total Knee System With Your Universal Instrument Technique", Johnson & Johnson, Inc., New Brunswick, N.J., No. OS-140 8/85 10M SP (1985) 2 pages.
Brochure, "17 MICROLOC(TM) Porous Coated Knee System Surgical Technique", Johnson & Johnson, Inc., New Brunswick, N.J., No. OT-140-10/84 10M C.P., (1984), 18 pages.
Brochure, "New Jersey Tricompartmental Total Knee System With PUROCOAT(®)—Surgical Procedure", DePuy, Warsaw, Ind., No. 7.5 M1084 0601-71 (Rev. 1) (1984), 22 pages.

*Primary Examiner*—C. Fred Rosenbaum
*Assistant Examiner*—Ralph Lewis
*Attorney, Agent, or Firm*—Susan M. Cornwall

[57] ABSTRACT

The present invention relates to a distal femoral surface shaping guide for mounting on an intramedullary alignment guide which references the central long axis of the femur in shaping the distal femoral surface and a method for shaping the distal femur using that shaping guide. The alignment guide of the present invention is adjustable relative to the surface of the anterior femoral cortex to insure that the anterior aspect of the distal femoral condyles is resected relative to that surface and, preferably, at the same level as that surface. The alignment guide of the present invention provides a main body which remains attached to the intramedullary alignment guide throughout the entire shaping of the distal femur. It thus requires fewer cutting guides and alignment steps than other shaping guides while allowing greater accuracy in shaping the distal femur relative to the central long axis of the femur.

12 Claims, 16 Drawing Figures

FEMORAL SURFACE SHAPING GUIDE FOR KNEE IMPLANTS

BACKGROUND OF THE INVENTION

This invention relates to a method and apparatus for shaping the distal surface of a human femur employing a novel adjustable shaping guide which is fixed to an intramedullary alignment guide which aligns with the central long axis of the femur.

In replacing a knee joint which has been damaged due to disease or trauma, it is very important that the prosthesis used to replace the damaged portion of the joint be properly aligned with respect to the bone to which the prosthesis is fixed. To enable a surgeon to shape the distal femur to receive a femoral component of a total knee joint prosthesis, Leo A. Whiteside, one of the named inventors herein, developed a method and apparatus for shaping a distal femoral surface which is claimed in U.S. Pat. No. 4,474,177 (issued 10/2/1984). That '177 Patent is hereby incorporated by reference to teach the use of an intramedullary alignment guide which provides the surgeon with a means for determining the central long axis of the femur and a means by which the surgeon can shape the distal femur relative to that axis by attaching distal femoral shaping instruments to that alignment guide. The '177 Patent teaches the use of a number of shaping guides to accomplish the shaping of the distal femoral surface. A more detailed surgical procedure describing this method of shaping the distal femur is described in Brochure No. L095-0201 9/85 entitled "Whiteside ORTHOLOC (TM) Total Knee System" from Dow Corning Wright Corporation, Arlington, TN (1985). Specific examples of two such shaping guide instruments described in that brochure (A/P Bevel Cutting Guide and Distal Cutting Guide) are shown in Brochure No. L095-PN003 entitled "New Whiteside ORTHOLOC (TM) Total Knee Instruments" also by Dow Corning Wright Corporation.

The shaping guide instruments described in the above patent and brochure lock onto the handle of the alignment guide and take their alignment from the position of the alignment guide handle. The surgeon selects the size of the prosthesis needed and a Standard, Large or Extra Large A/P Bevel Cutting Guide is fixed to the handle and the distal femoral surface is shaped using the guide surfaces on the Cutting Guide. The Distal Cutting Guide is adjustable to permit resection of the distal femoral condyles over a range of 6-10 millimeters. However, once the cutting guide is attached to the handle of the alignment guide, the guide surfaces on the cutting guide cannot be adjusted relative to the handle and thus relative to the surfaces of the femur being shaped. It is quite important that the anterior aspect of the distal femoral condyles be shaped relatively even with the anterior femoral cortical surface.

Brochure No. 86-038-5780-0525/16MA (1986) from Zimmer, Inc., Warsaw, Ind., entitled "ZIMMER (R) Intramedullary Knee Instrumentation For the Miller Galante Total Knee System" shows an Anterior Femoral Cutting Guide Instrument No. 5785-018 which uses a locator to reference the anterior femoral cortical surface and thus guide resection of the anterior aspects of the femoral condyles relative to that anterior cortical surface. That Guide Instrument is mounted on a Femoral IM (intramedullary) Alignment Guide No. 5785-012. However, the other distal femoral surfaces are then shaped after the IM Alignment Guide is removed from the femur and several different shaping guides are employed to accomplish the shaping of the femur.

Androphy, in U.S. Pat. No. 4,487,203 (issued 12/11/84), teaches a triplanar knee resection method which employs a single cutting guide member which is used in conjunction with L-shaped femur and tibia guide rods which are placed in the intramedullary canal to accomplish the shaping of the distal femur and the proximal tibia. The anterior and posterior aspects of the femoral condyles are shaped using the cutting guide member locked onto the L-shaped guide rod while the distal femoral condyles are shaped to a particular degree (based on a flexion gap determination) using a slidably adjustable bar which moves the cutting guide relative to the femoral guide rod.

Brochure No. 81-038-226-1020/15MZ entitled "Knee Replacement Using The INSALL/BURSTEIN Total Condylar Knee System" from Zimmer, Inc., Warsaw, IN (1981) teaches the use of a femoral hole locator which references the anterior femoral cortical surface to locate a point where a drill is used to provide an opening for a rod on which a separate femoral surface shaping guide is mounted. The shaping guide itself is not adjustable relative to the rod once the guide is mounted on the rod.

Lacey, in U.S. Pat. No. 4,502,483 (issued 3/5/1985), teaches a method and apparatus for shaping a distal femoral surface which uses an external alignment guide which has a main body which mounts on the surface of the anterior femoral cortex and employs femoral surface shaping guides whose shaping guide surfaces are adjusted relative to certain points on the distal femoral surface using locator pins. One such locator pin references the anterior surface intercondylar notch to align the shaping guide surfaces for shaping the anterior and posterior aspects of the distal femoral condyles. No intramedullary alignment guide is used with this apparatus.

Other examples of shaping guides which reference the anterior femoral cortical surface to accomplish the shaping of the posterior and anterior aspects of the distal femoral condyles can be found on pages 9-10 of Brochure No. 3246 Rev. 9-79 entitled "R.M.C. Total Knee System—Technique" from Richards Manufacturing Co., Inc., Memphis, TN (1979) and on page 14 and 20-12 of Brochure No. B-260-1 10M778 entitled "GEO-PATELLA (TM)/GEO-TIBIAL (TM) Total Knee —Surgical Technique" from Zimmer, Inc., Warsaw, IN (1977). Neither of these instruments employ intramedullary alignment guides to provide a reference point for the shaping guides.

In all of the above methods, multiple sets of shaping guides are generally employed to shape the distal femur.

SUMMARY OF THE INVENTION

One object of the present invention is to provide a simple method and apparatus for shaping the distal femur to receive the femoral component of a total knee prosthesis using a distal femoral shaping guide which is designed to be fixed to an external support means present on (e.g., the handle of) an intramedullary alignment guide so that shaping can be done relative to the central long axis of the femur using one shaping guide to which all shaping guides are attached or are present thereon. The primary object is to minimize the number of shaping instruments and alignment procedures necessary for knee joint replacement by providing a surgeon with a shaping guide which has a main body that is attached and aligned once during the surgical procedure and on which all other shaping guides are mounted; the main body remains attached to the alignment guide handle throughout the entire shaping procedure.

It is another object of the present invention to provide a shaping guide which is adjustable with respect to the anterior femoral cortex surface to permit accurate shaping of the anterior and posterior aspects of the distal femoral condyles using a single external point of reference as well as the central long axis of the femur as points of reference for all shaping operations. The invention also provides a stabilizing means for fixedly securing the cutting guide to the sides of the distal femur to retain that alignment.

The shaping guide of the present invention is adjustable with respect to the handle of the alignment guide so that an anterior femoral cortical surface feeler gauge which is fixed to the surface of the main body comprising the shaping guide can be used to raise or lower the cutting guide surfaces to permit the anterior aspect of the femoral condyles to be shaped relative to, and preferably even with, the level of the anterior femoral cortical surface. The main body of the shaping guide which attaches to the handle of the alignment guide remains fixed to the handle after the main body is adjusted relative to the anterior femoral cortex during the entire shaping procedure. The main body further contains a stabilizing means for fixing the main body to one side of the distal femur after the main body is adjusted relative to the anterior femoral cortex surface. The upper surface of the main body which faces anteriorly relative to the femur contains an attachment means to which the feeler gauge and other shaping guides can be attached to accomplish shaping of the distal femoral surface. Preferably, the main body contains at least one shaping guide surface formed as a part of the main body. It is preferred that the main body contain integrally formed shaping guide surfaces for shaping the anterior and posterior aspects of the distal femoral condyles and, more preferably, further contain bevel cutting guide surfaces.

In an alternative embodiment, the main body contains all shaping guide surfaces required to complete the shaping of the distal femoral surfaces formed as an integral part of the main body and no further shaping guides need be attached to the main body during the process of shaping the distal femur.

BRIEF DESCRIPTION OF THE DRAWINGS

The above and other objects, features, and advantages of the present invention will become apparent to those skilled in the art upon an examination of the following description and drawings which are illustrative of the present invention. In the Drawings.

DETAILED DESCRIPTION OF THE INVENTION

Referring to the Drawings, particularly FIGS. 1–5 and 8–10, the preferred embodiment of the apparatus of the present invention is shown as distal femoral condyle shaping guide 10 composed of main body 12 having upper surface 14 which faces in the direction of the anterior aspect of right femur 80 (while references will be made to the right femur, the invention also applies to the same type of guide used for the left femur) when guide 10 is fixed to handle 88 of intramedullary alignment guide 82 as shown in FIGS. 8–13. Upper surface 14 contains an attachment means in the form of two threaded studs, 15 and 16, which extend up away from surface 14. Main body 12 contains a means 18 by which main body 12 can be rigidly fixed to handle 88 in the form of two opposed knurled cap bolts 19 and 20 which serve to both grasp planar surfaces 88' and 88" of handle 88 as a result of contact with flat surfaces 24 and 25 of bolts 19 and 20, respectively. Opening 22 in main body 12 permits viewing of the level at which main body 12 engages handle 88. Reference marks indicated at 28 are inscribed on front face 11 of main body 12 to better enable a surgeon to determine that level and thus the level at which shaping means guide surfaces associated with main body 12 are located relative to guide 82. Studs 15 and 16 have reference marks 28' corresponding to reference marks 28 to better permit the surgeon to determine the proper setting of main body 12. In the embodiment shown, the means by which the main body is fixed to guide 82 and the means by which the level of main body 12 is adjusted relative to guide 82 are one and the same although other embodiments may contain a separate means for grasping handle and a separate level adjustment means such as a sliding central portion permitting up and down (anterior and posterior) movement of the portion of the main body containing or holding the shaping means guide surfaces.

Figure 1:
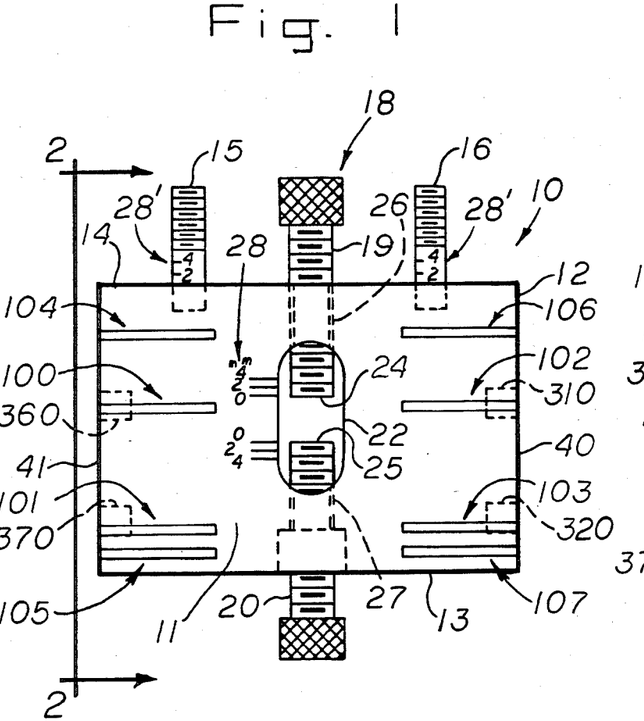
FIG. 1 is a front view of main body 12 of the femoral shaping guide 10 of the present invention.
Figure 2:
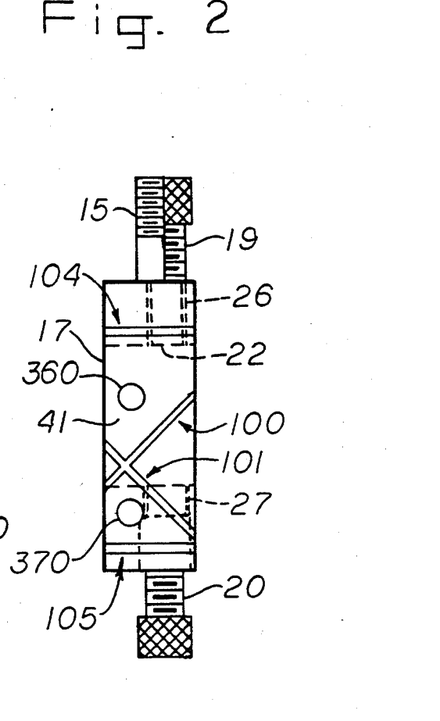
FIG. 2 is a left side view of FIG. 1.
Figure 3:
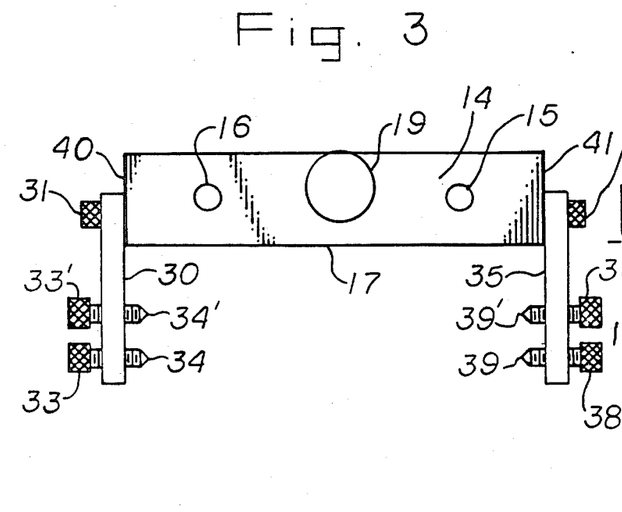
FIG. 3 is a plan view of main body 12 of FIG. 1 which further contains side stabilizing members 30 and 35.

Main body 12 contains two sets of shaping means guide surfaces formed as a part of the main body as opposed to a separately attachable shaping guide such as guide 60. Thus, main body 12 contains anterior condyle shaping means guide surfaces 104 and 106, posterior condyle shaping means guide surfaces 105 and 107, and bevel condyle shaping means guide surfaces 100, 101, 102 and 103.

Threaded bores 310 and 320 on medial side surface 40 of main body 12 and corresponding threaded bores 360 and 370 on lateral side surface 41 engage knurled cap bolts 31, 32, 36 and 37 to permit members 30 and 35 to be fixed to each respective side of main body 12 when the bolts are passed through bores in each member. Stabilizing member 30 contains two threaded, knurled cap bolts 33 and 33' each passing through a threaded bore in the end of member 30 opposite main body 12 and each comes to point 34 and 34', respectively. Stabilizing member 35 contains the same type of bolts 38 and 38' coming to point 39 and 39', respectively. One of members 30 and 35 are employed to fix main body 12 rigidly to distal femur 80 as will be described, infra.

Figure 4:
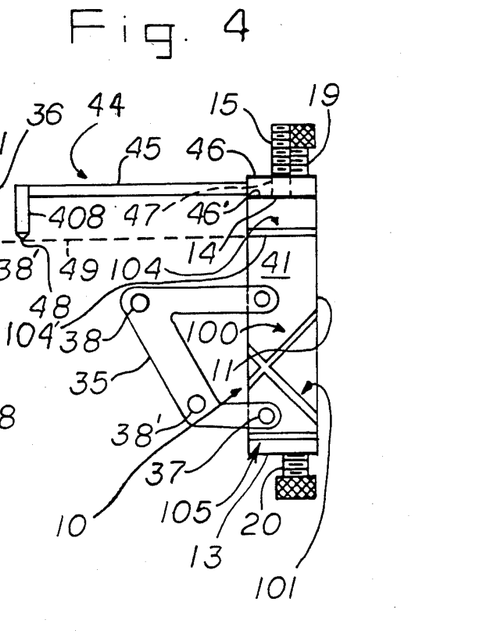
FIG. 4 is a right side view of guide 10 of FIG. 3 further showing an anterior femoral cortical surface feeler gauge 44 mounted over studs on upper surface 14 of main body 12.
Figures 5, 5A:
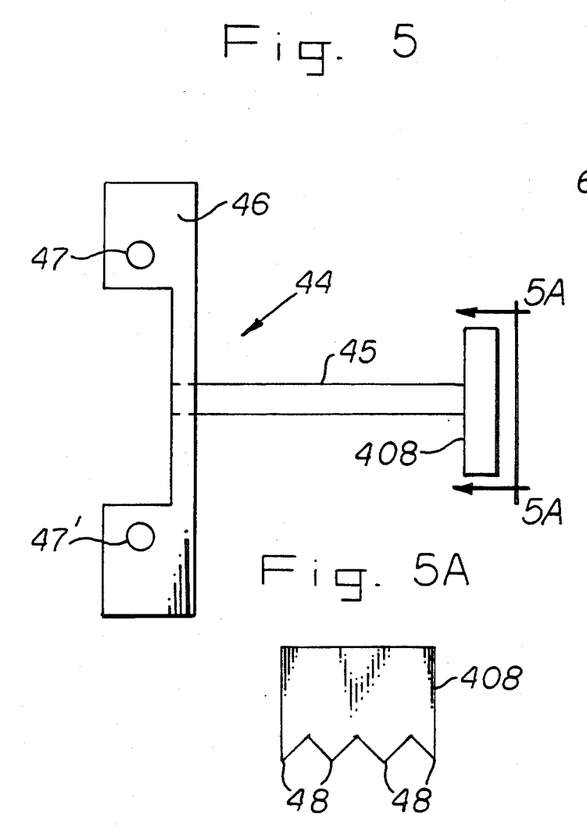
FIG. 5 is a plan view of anterior femoral cortical surface feeler gauge 44 and FIG. 5A shows a front view of indicator 408.

FIGS. 4 and 5 show anterior cortical surface feeler gauge 44 which is composed of a base 46 having an L-shaped pointer 45 extending away from base 46 and terminating in blade-shaped indicator 408 having a several points 48. The blade-like elongated configuration of indicator 408 with several points 48 is preferred over a pointer with a single point since handle 88 is often set at an angle with respect to rod portion 84 to provide the desired valgus angle and this may cause a feeler gauge with a single point to contact cortical surface 81 at a point other than at the apex of the anterior cortical surface 81. Because of its blade-like shape, the lower edge of indicator 408 can push through soft tissue overlying surface 81 and insure that actual contact with the apex of surface 81 is made.

Base 46 contains two smooth bores 47 and 47' which permit base 46 to be rigidly mounted over studs 15 and 16. Base 44 is constructed such that when base 44 is mounted on upper surface 14 of main body 12 and lower surface 46' of base 44 contacts surface 14, point 48 lies on a line 49 which is parallel with and at the same level as lower surface 104' and 106', respectively, of shaping means guide surfaces 104 and 106.

Figure 6:
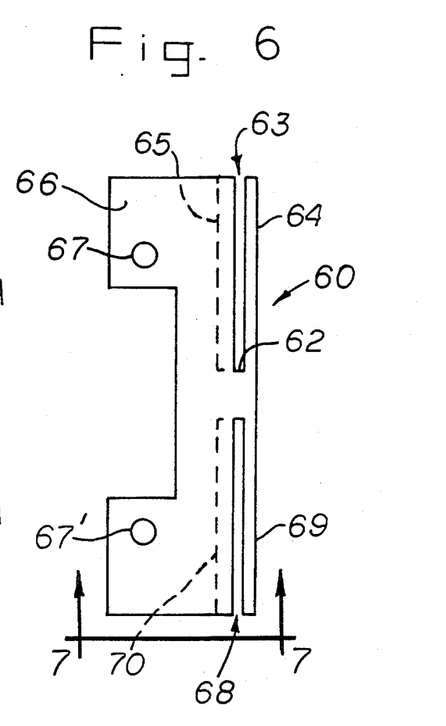
FIG. 6 is a plan view of a distal femoral condyle shaping guide 60 which also fits over the studs 15, 16 in main body 12.
Figure 7:
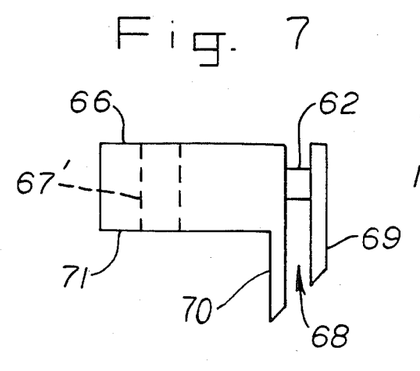
FIG. 7 is a left side view of FIG. 6.

FIGS. 6 and 7 show distal femoral surface shaping means guide 60 which is composed of base 66 containing two smooth bores 67 and 67' which permit base 46 to be rigidly mounted over studs 15 and 16. A distal femoral surface shaping guide means composed of guide 63 is formed by metal guideplates 64 and 65 and guide 68 is formed by metal guideplates 69 and 70. Guide plates 65 and 70 are attached to base 66 and are separated from guide plates 64 and 69 by bar 62. Guideplates 65 and 70 as well as guideplates 64 and 69 can each be one continuous plate. The distance between the center of centrally mounted studs 15 and 16 and the surfaces of guides 63 and 68 on which the femoral surface shaping means is to rest (e.g., an oscillating saw blade) is selected to suit the amount of distal femoral condyle surface necessary to be removed to properly fit a femoral component of a knee prosthesis on femur 80. If desired, but less preferable, separate guides for shaping, for example, the anterior and posterior aspects of the distal femoral condyles could also be made similar to that described for guide 60 using appropriately oriented cutting guide surfaces instead of including such guide surfaces as part of the main body.

Figure 13:
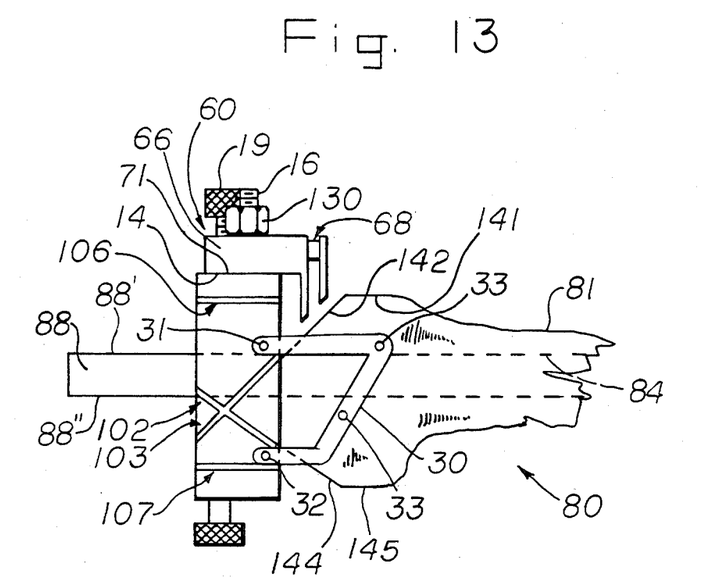
FIG. 13 shows distal femoral condyle shaping guide 60 fixed to studs 19 and 20 of main body 12 ready to accomplish resection of the distal condyles after the other portions of distal femur 80 have been shaped.

As shown in FIG. 13, the lower edges of guide plates 64, 65, 69 and 70 come rather close to the bevelled surface 142 Of femur 80 to insure that a saw blade is accurately guided in shaping the distal femoral condyles. This configuration along with a removable shaping guide such as guide 44 is preferred where the surgeon desires to shape the distal femur to receive a prosthesis which is affixed to the femur via bone ingrowth into a porous substrate such as sintered metal beads as opposed to fixation by cementing the prosthesis to the distal femur. This configuration provides the very accurate degree of shaping of the distal femur needed for such implants and in such a case, it is preferred that the distal femoral condyle shaping step be done last to provide clearance for the lower edges of guide 60.

Figure 15:
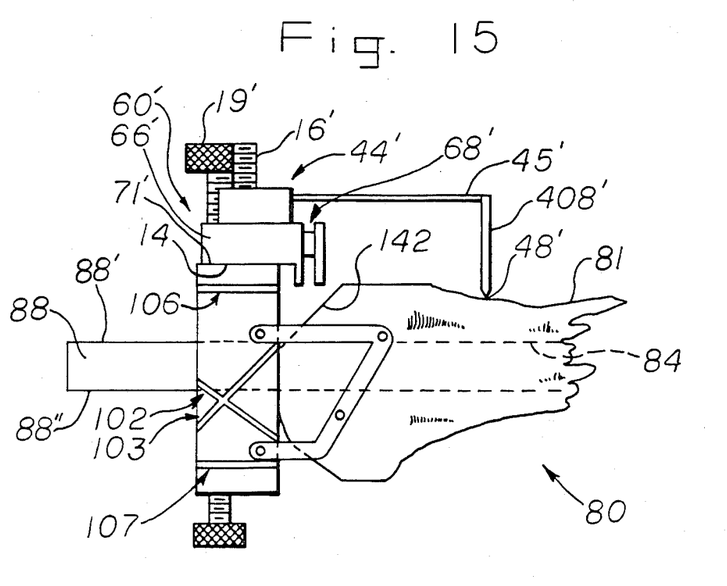
FIG. 15 shows an alternative embodiment of the invention fixed to handle 88 wherein the main body has a distal femoral condyle shaping guide 60' fixed thereto and feeler gauge 44' placed on top of guide 60'.

If the prosthesis to be implanted is to be cemented to the femur, the layer of cement can fill in minor inconsistencies in surface shaping. In that case, the distal femoral shaping guide 60 can be made as a fixed part of main body 12 (e.g., extend the length of studs 15 and 16, fix guide 60 to the top surface 14, and modify feeler gauge 44 so that points 48 line up with line 49 as shown in FIG. 4) to provide a shaping guide with all shaping means guide surfaces integral with main body 12. In that embodiment, shown in FIG. 15 the lower edges of the distal femoral shaping means guide would not extend as close to the femur as shown for guide 60 since the main body would be attached to the handle before the distal femur is shaped and clearance would be needed between the femur and those lower surfaces. Due to the clearance, there would be more opportunity for a saw blade to waver and the shaped surface may not be as even as is needed for porous ingrowth fixation prostheses, but would be satisfactory for prostheses using cement fixation. In this embodiment, all shaping means guide surfaces are located on the main body which is not removed until all shaping operations are completed.

The above described main body, intramedullary alignment guide, feeler gauge, shaping means guide, and associated components are all preferably manufactured from a suitable surgical grade of stainless steel or other metal commonly employed by those skilled in the art to construct surgical tools for use in contact with the body. The exact composition of the materials used to construct the above forms no part of the present invention as long as it performs the desired function; other materials suitable for use within the body and for the intended uses of the above may be used without altering the nature of the invention.

The manner in which the apparatus of the present invention may be used will now be described with reference to FIGS. 8–14. The present invention relies on the use of an intramedullary alignment guide to reference the shaping of the distal femur to the central long axis of the femur as defined by that intramedullary alignment guide. The preferred intramedullary alignment guide employed in conjunction with the present invention is that described in the Whiteside '177 Patent which has been incorporated by reference herein and the manner in which that intramedullary alignment guide is used is further described in the Dow Corning Wright brochures noted above. While the type of intramedullary alignment guide and manner of placing it within the intramedullary canal preferred is that of the Whiteside '177 Patent type, other intramedullary alignment guides can be employed with the shaping guide of the present invention provided that the shaping guide of the present invention can be attached to such an alternative alignment guide in such a way as to permit shaping of the distal femoral surface relative to the central long axis of the femur as defined by the alignment guide. The intramedullary alignment guide may be inserted within the femur using various guides to direct the surgeon as to where to place the boring tool used to create a passage for the intramedullary alignment guide, e.g., a guide such as the femoral hole locator tool described in Zimmer Brochure No. 81-038-226-1020/15MZ noted above could be used to define the entry point for the intramedullary alignment guide, even in conjunction with the Whiteside '177 Patent method. The type of intramedullary alignment guide employed and the manner in which it is placed within the femur is conventional and forms no part of the present invention.

Figure 8:
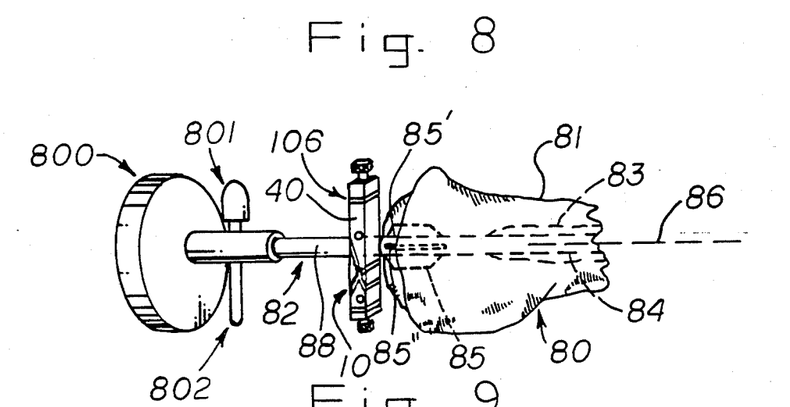
FIG. 8 is a side perspective view showing intramedullary alignment guide 82 being inserted into the intramedullary canal of femur 80 using main body 12 as a rotational alignment guide.

FIG. 8 shows intramedullary alignment guide 82 of the same type which is described in the Whiteside '177 patent being placed within a bore in femur 80 running through the intramedullary canal 83 defined by the wall 81 of cortical bone making up femur 80. The bore has been prepared in accordance with the Whiteside method such that central long axis 86 of the intramedullary rod portion 84 of guide 82 is concentric with the central long axis of femur 80 after the rod portion 84 which contains 3 locking fins 85, 85' and 85" has been inserted to its full length (i.e., approximately up to the point where handle 88 is joined to rod portion 84) within the bore in femur 80. Guide 82 is selected such that handle 88 is set at an angle relative to axis 86 to provide the desired degree of valgus angle the surgeon wishes to obtain on the knee prosthesis after implantation.

Main body 12 has been fixed to handle 88 by tightening bolts 19 and 20 down over surfaces 88' and 88" of handle 88 such that the handle is centered between the zero markings of reference markings 28. In accordance with the Whiteside method, impactor 800 has been locked to handle 88 by means of locking pin 801 having portion 802 which passes through bores in impactor 800 and handle 88 and intramedullary alignment guide 82 has been inserted within the bore in femur 80 up to the point where fins 85, 85' and 85" almost touch the distal surface of femur 80. The rotational alignment of guide 82 is adjusted using the lower surface 13 of main body 12 as a guide in accordance with the Whiteside method to visualize equal amounts of the posterior aspects of the condyles on a plane running parallel with surface 13. This aligns guide 82 because surfaces 88' and 88" are parallel with surface 13. Guide 82 is then driven into the femur using a mallet on the impactor 800 until fins 85, 85' and 85" are embedded in the cortical bone of the distal femur. Impactor 800 and pin 801 are removed and the method of the present invention is begun.

Figures 9, 10:
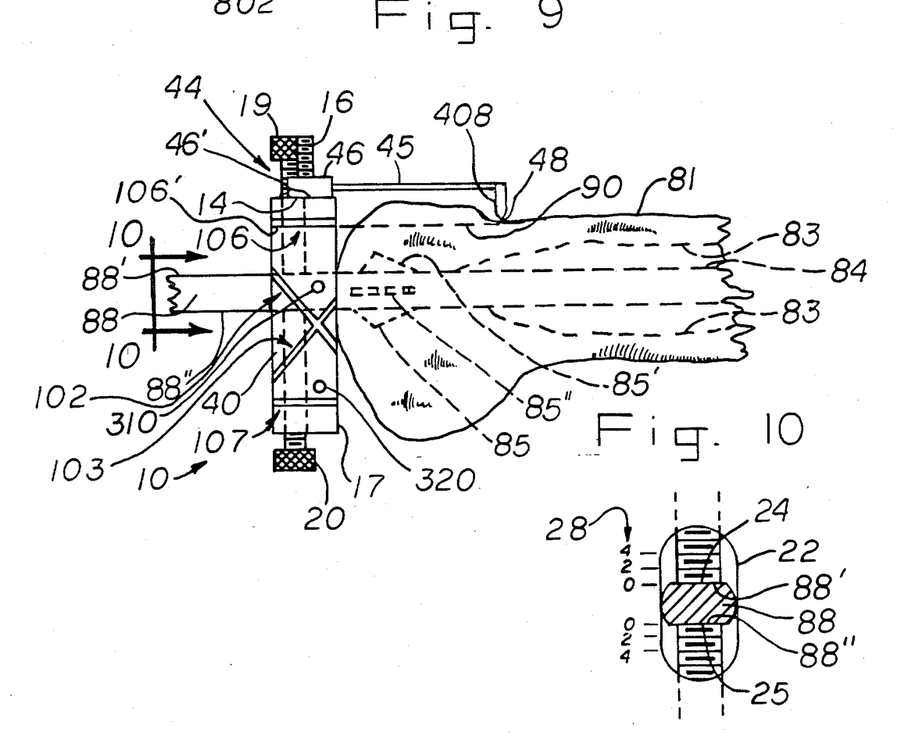
FIG. 9 shows main body 12 fixed to handle 88 of intramedullary alignment guide 82 and adjusted using feeler gauge 44 so that the lower guide surface 106, of guide 106 is level with anterior femoral cortical surface 81.
FIG. 10 is a partial front view taken in the direction of arrows 10—10 of the adjustment markings 28 showing the alignment of main body 12 relative to the intramedullary alignment guide 82 and to anterior femoral cortical surface 81.

With guide 12 locked on handle 88 as described above and with back surface 17 resting against the distal condyles of femur 80, feeler gauge 44 is placed over studs 15 and 16 and allowed to slide down until points 48 of indicator 408 rest on the anterior femoral cortical surface 81. Preferably, main body 12 and feeler gauge 44 are constructed such that when surfaces 88' and 88" are centered between the zero reference markings 28, points 48 come in contact with surface 81. The surgeon can observe the markings 28' on studs 15 and 16 in making this alignment. This permits the surgeon to shape the anterior aspect of the distal femoral condyles level with surface 81. The posterior aspects of the distal femoral condyles will also be shaped relative to surface 81 since guide surfaces 105 and 107 are part of main body 12.

Figure 11:
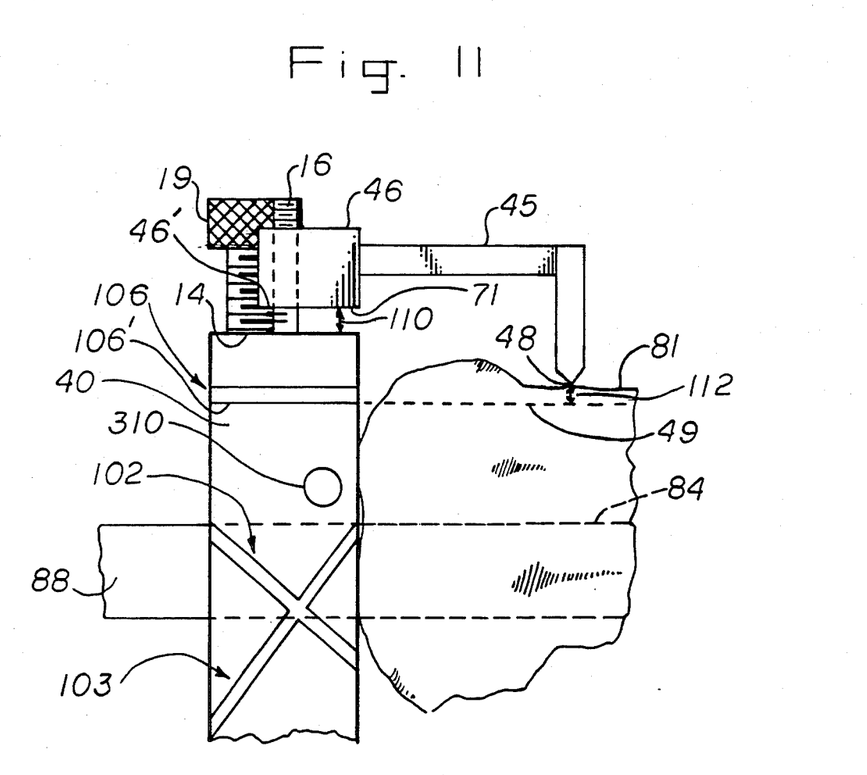
FIG. 11 is an enlarged partial side view of main body 12 and feeler gauge 44 showing how a misalignment with respect to the anterior femoral cortical surface 81 is indicated.

FIG. 11 shows the effect of having main body 12 and thus guide surface 106 too low with respect to anterior femoral cortical surface 81. A space indicated by arrows 110 can be seen between surfaces 46' and 14 which is equal to the distance between point 48 which is resting on surface 81 and line 49 which is at the same level as surface 106' of guide surface 106. If desired for some reason such as an anatomical defect, the surgeon could conduct the shaping of the distal femoral surface at this setting of the main body. Preferably, bolts 19 and 20 would be turned by the amount indicated by markings 28' on studs 15 and 16 until the space between surfaces 46' and 14 was eliminated thereby indicating that line 49 and thus, surface 106', was at the same level as surface 81. If main body 12 was set at too high of a level relative to surface 81, the surgeon would observe that point 48 was not in contact with surface 81 and would lower main body 12 using bolts 19 and 20 until point 48 just contacts surface 81. This procedure provides this method with an advance over the Whiteside '177 Patent in that the femur can be shaped relative to the level of anterior femoral cortical surface as well as with respect to the central long axis of the femur. Feeler gauge 44 is then removed and stabilizing member 30 is fixed to (for the case of a right femur shown in the Drawings) the medial side 40 of main body 12 using bolts 31 and 32. Member 35 which would be placed on the lateral side 41 of the main body is not used because the patella is moved to the lateral side during this shaping procedure. Bolt 33 is then tightened until point 34 securely contacts the medial side of femur 80 and thereby fixes main body 12 securely to distal femur 80. It is understood that members 30 could have been present on main body 12 during the above alignment procedure and bolt 33 tightened after main body 12 was leveled. Member 35 is used in place of member 30 using the bolts shown for that member 35 if guide 10 was being used to shape the left distal femur. Other stabilizing means could be used to fix main body 12 to the distal femur 80 provided that such stabilizing means does not interfere with the shaping means used to shape the distal femur. The advantage of using a stabilizing member is that it prevents rotation and loosening of main body 12 from handle 88 and reduces the tendency of guide 82 to back out of femur 80 as a result of the use of a shaping means such as an oscillating saw. A further advantage is that other alignment guides which fix to the end of the distal femur via pins driven within the bone can disrupt the integrity of the bone, particularly where the bone is osteoporotic and already weak in structure as is often the case with older patients.

Figure 12:
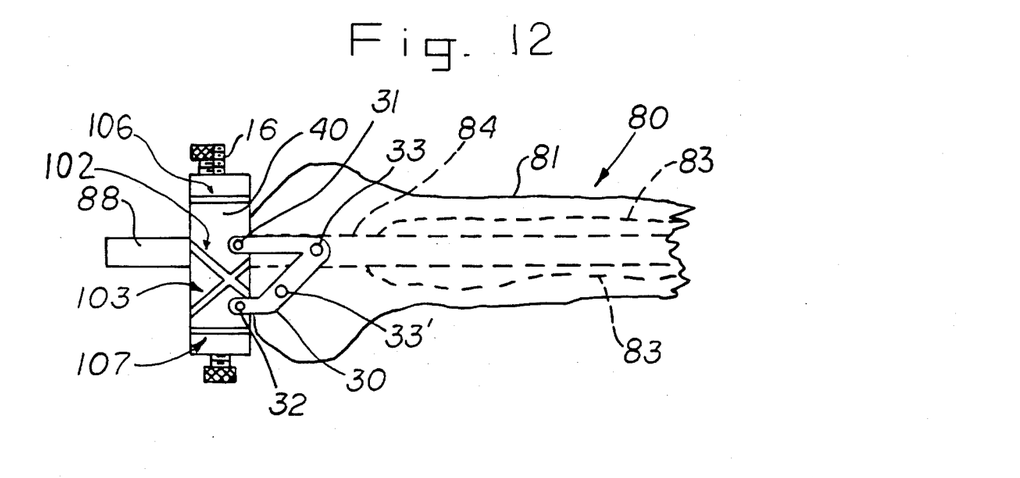
FIG. 12 is a side view showing main body 12 secured to the medial side of femur 80 by member 30 and ready for shaping of femur 80 using the guide surfaces thereon.

After fixing main body 12 to distal femur 80, a conventional shaping means such as an oscillating saw or a hand saw (not shown) is then introduced between guide surfaces 104 and 106 to resect the anterior aspect of the distal condyles to produce surface 141, between guide surfaces 105 and 107 to resect the posterior aspects of the distal femoral condyles to produce surface 145, between bevel guide surfaces 101 and 103 to produce surface 142 and between bevel guide surfaces 102 and 104 to produce surface 144.

Figure 14:
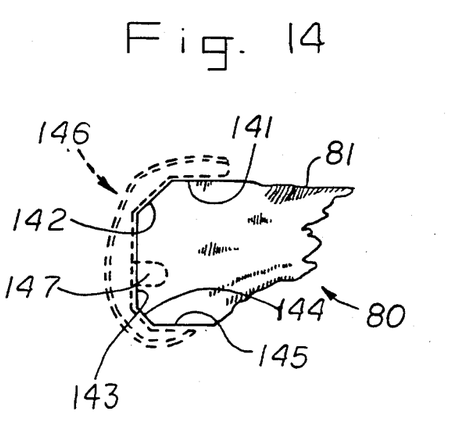
FIG. 14 is a side perspective view of shaped femur 80 with a distal femoral component 146 of a knee joint prosthesis shown in relief over the shaped surface.

The angles of the shaping guide surfaces relative to the distal femur and the number thereof are selected to match the prosthesis to be fixed to the distal femur as shown in FIG. 14 for femoral component 146 having post 147 and a second such post opposite post 147 (not shown) used to assist in fixing component 146 to the distal femur after shaping is complete. Main body 12 may further contain bores or other guide means to assist the surgeon in placing bores in the distal femur for posts such as post 147.

One more shaping operation is necessary to complete the shaping of distal femur 80 using the above procedure. After the above shaping steps are completed, distal femoral condyle shaping means guide 60 is placed over studs 15 and 16 and surface 71 is brought up against surface 14 of main body 12. A threaded nut 130 or a wingnut is placed on stud 16 and used to secure base 66 to the upper surface 14 of main body 12 and a similar means is used to secure base 66 to stud 15. A shaping means such as an oscillating saw or a hand saw is placed in guide surface 68 to resect the medial distal condyle perpendicular to the central long axis of femur 80 and guide surface 63 is similarly employed to resect the lateral distal condyle in the same manner to result in creation of shaped surface 143 on distal femur 80.

Shaping of the distal femur in accordance with the method of the present invention is now completed, bolt 33 is released from the side of femur 80, and the intramedullary alignment guide is removed along with main body 12. Main body 12 has remained attached to the alignment guide during the entire shaping procedure thus maintaining its original alignment throughout the entire procedure thus using the same reference points (anterior femoral cortical surface and central long axis of the femur) during the entire procedure. As noted, the left distal femur can be shaped in the same manner using the same guide 10. Guide 10 can be used to shape the distal femur to receive a number of different femoral components simply by selecting appropriately oriented guide surfaces in the main body and/or guides which are capable of being attached to the main body. It is also contemplated that the anterior aspects of the femoral condyles need not be the first to be resected and that the distal femoral surfaces can be shaped in any order desired except as described above for shaping the femur to receive porous ingrowth fixation prostheses.

Other modifications of the apparatus and method of the present invention will become apparent to those skilled in the art from an examination of the above specification and drawings. Therefore, other variations of the present invention may be made which fall within the scope of the following claims even though such variations were not specifically discussed above.

That which is claimed is:

1. A distal femoral surface shaping guide for fixation to an intramedullary alignment guide having (a) an intramedullary alignment rod portion which is fixed within the intramedullary canal of a femur in such a manner as to have the central long axis of the rod concentric with the central long axis of said femur and (b) an external support means attached to said rod portion in an aligning relationship with respect to the central long axis of the rod portion, said shaping guide comprising, in combination, (A) a main body having an upper surface facing anteriorly with respect to the distal femur when the main body is fixed to the alignment guide, a means for cooperatively engaging said external support means, an adjustable means for fixing said main body in proper alignment with respect to the central long axis of the intramedullary rod portion, a stabilizing means for fixing the main body to the distal femur, and an attachment means fixed to said main body, (B) an anterior femoral cortical surface feeler gauge which cooperatively engages said attachment means and, when engaged, is movable relative to said main body and indicates the amount a shaping means guide surface for shaping the anterior aspect of the femoral condyles is improperly aligned with respect to the upper surface of the anterior femoral cortex so that the adjustable means may be adjusted until said main body is in proper anterior/posterior alignment, and (C) a sufficient number of distal femoral surface shaping guides having shaping means guide surfaces thereon which guides cooperatively engage said attachment means to ultimately permit complete shaping of the distal femur in such a manner that a preselected femoral knee prosthesis can be attached to the shaped distal femur, said feeler gauge and said surface shaping guides cooperatively engaging said attachment means one at a time and said main body remaining fixed to the intramedullary alignment guide during the entire shaping process.

2. The distal femoral surface shaping guide as claimed in claim 1 wherein the main body further contains at least one shaping means guide surface formed as a part of said main body.

3. The distal femoral surface shaping guide as claimed in claim 2 wherein the main body contains shaping means guide surfaces for shaping the anterior and the posterior aspects of the distal femoral condyles.

4. The distal femoral surface shaping guide as claimed in claim 3 wherein the main bodY further contains a plurality of bevel shaping means guide surfaces situated at an appropriate angle with respect to a flattened shaped distal femoral surface such that a portion of the anterior and posterior aspects of the distal femoral surface can be shaped to produce a suitably bevelled distal femoral surface.

5. The distal femoral surface shaping guide as claimed in claim 3 wherein the shaping guide of (C) comprises a base for cooperatively engaging said attachment means having a first and a second femoral surface shaping guide surface extending a preselected distance away from said base over the distal femoral surface to be shaped, each of said first and second surfaces being oriented so as to shape the medial and lateral aspects of the distal femoral condyles relative to the central long axis of the femur.

6. The distal femoral surface shaping guide as claimed in claim 1 wherein the means for fixing the main body to the distal femur consist of a side member for mounting on one side of said main body, said member having a first end which is releasably fixed to the side of the main body and an opposite end which contains a grasping means for securing said member to the side of said distal femur.

7. The distal femoral surface shaping guide as claimed in claim 1 wherein said means for cooperatively engaging said external support means and said adjustable means are one and the same.

8. A distal femoral surface shaping guide for fixation to an intramedullary alignment guide having (a) an intramedullary alignment rod portion which is fixed within the intramedullary canal of a femur in such a manner as to have the central long axis of the rod concentric with the central long axis of said femur and (b) an external support means attached to said rod portion in an aligning relationship with respect to the central long axis of the rod portion, said shaping guide comprising, in combination, (A) a main body having an upper surface facing anteriorly with respect to the distal femur when the main body is fixed to the alignment guide, a plurality of femoral surface shaping guide surfaces formed as part of the main body, a means for cooperatively engaging said external support means, an adjustable means for fixing said main body in proper alignment with respect to the central long axis of the intramedullary rod portion, a stabilizing means for fixing the main body to the distal femur, and an attachment means fixed to said main body, and (B) an anterior femoral cortical surface feeler gauge which cooperatively engages said attachment means and, when engaged, is movable relative to said main body and indicates the amount a shaping means guide surface for shaping the anterior aspect of the femoral condyles is improperly aligned with respect to the upper surface of the anterior femoral cortex so that the adjustable means may be adjusted until said main body is in proper anterior posterior alignment; wherein said main body contains a sufficient number of femoral surface shaping means guide surfaces to ultimately permit complete shaping of the distal femur in such a manner that a preselected femoral knee prosthesis can be attached to the shaped distal femur, said main body remaining fixed to the intramedullary alignment guide during the entire shaping process.

9. The distal femoral surface shaping guide as claimed in claim 8 wherein the means for fixing the main body to the distal femur consists of a side member for mounting on one side of said main body, said member having a first end which is releasably fixed to the side of the main body and an opposite end which contains a grasping means for securing said member to the side of said distal femur.

10. The distal femoral surface shaping guide as claimed in claim 8 wherein said means for cooperatively engaging said external support means and said adjustable means are one and the same.

11. A method of preparing a human femur having a distal femoral surface containing medial and lateral condyles and an intramedullary canal located at the center of a tubular shaft of hard compact bone to receive a distal femoral knee prosthesis, said femur having fixed therein an intramedullary alignment guide having (a) an intramedullary alignment rod portion which is fixed within the intramedullary canal of a femur in such a manner as to have the central long axis of the rod concentric with the central long axis of said femur and (b) an external support means attached to said rod portion in an aligning relationship with respect to the central long axis of the rod portion, said method comprising the steps of (I) fixing to said external support means one component of a distal femoral surface shaping guide, said component being a main body having an upper surface facing anteriorly with respect to the distal femur when the main body is fixed to the alignment guide, a means for cooperatively engaging said external support means, an adjustable means for fixing said main body in proper alignment with respect to the central long axis of the intramedullary rod portion, a means for fixing the main body to the distal femur, and an attachment means fixed to said main body, said main body optionally containing at least one femoral surface shaping means guide surface formed as an integral part of the main body, (II) engaging to said attachment means an anterior femoral cortical surface feeler gauge which cooperatively engages said attachment means and indicates when a shaping means guide surface for shaping the anterior aspect of the femoral condyles is properly aligned with respect to the upper surface of the anterior femoral cortex, (III) adjusting said adjustable means to bring said main body in proper alignment with respect to the upper surface of the anterior femoral cortex, (IV) fixing said main body to the distal femur with said stabilizing means, (V) Removing said feeler gauge from said attachment means, and thereafter (VI) modifying said distal femur through the use of one of the distal femoral surface shaping means guide surfaces present as a part of said main body, (VII) modifying said distal femur using a digtal femoral surface shaping guide having shaping means guide surfaces thereon which guide cooperatively engages said attachment means, if said main body does not contain all distal femoral shaping means guide surfaces necessary to accomplish complete shaping of said distal femur, (VIII) repeating steps (VI) and (VII) as needed until an appropriately shaped distal femoral surface is obtained, and lastly, (IX) removing said main body and intramedullary alignment guide from the shaped femur, wherein said main body remains fixed to the intramedullary alignment guide during the entire shaping process.

12. The method as claimed in claim 11 wherein all distal femoral surface shaping means guide surfaces necessary to accomplish complete shaping of said distal femur are formed as an integral part of the main body and Step (VII) is omitted.

* * * * *